US 9,265,896 B2

(12) United States Patent
Uemura et al.

(10) Patent No.: US 9,265,896 B2
(45) Date of Patent: Feb. 23, 2016

(54) METHOD FOR MANUFACTURING PUNCTURE NEEDLE (71) Applicant: SHINMAYWA INDUSTRIES, LTD., Takarazuka-shi, Hyogo (JP)

(72) Inventors: Kensuke Uemura, Takarazuka (JP); G. Alexey Remnev, Takarazuka (JP); V. Konstantin Shalnov, Takarazuka (JP)

(73) Assignee: SHINMAYWA INDUSTRIES, LTD., Takarazuka (JP)

(*) Notice: Subject to any disclaimer, the term of this patent is extended or adjusted under 35 U.S.C. 154(b) by 62 days.

(21) Appl. No.: 14/377,235

(22) PCT Filed: Feb. 14, 2013

(86) PCT No.: PCT/JP2013/053493
§ 371 (c)(1),
(2) Date: Aug. 7, 2014

(87) PCT Pub. No.: WO2013/125430
PCT Pub. Date: Aug. 29, 2013

(65) Prior Publication Data
US 2016/0015908 A1    Jan. 21, 2016

(30) Foreign Application Priority Data
Feb. 23, 2012   (JP) ................................ 2012-036884

(51) Int. Cl.
| B21G 1/08 | (2006.01) |
| C23C 14/24 | (2006.01) |
| A61M 5/158 | (2006.01) |
| A61M 5/32 | (2006.01) |
| A61B 5/15 | (2006.01) |
| C23C 14/00 | (2006.01) |
| C23C 14/58 | (2006.01) |
| A61B 17/06 | (2006.01) |

(Continued)

(52) U.S. Cl.
CPC ........ *A61M 5/3286* (2013.01); *A61B 5/150282* (2013.01); *B21G 1/08* (2013.01); *C23C 14/0042* (2013.01); *C23C 14/5826* (2013.01); *A61B 5/150396* (2013.01); *A61B 5/150427* (2013.01); *A61B 2017/06071* (2013.01); *A61M 2207/00* (2013.01); *B21G 1/12* (2013.01); *C23C 8/06* (2013.01); *Y10T 29/49885* (2015.01)

(58) Field of Classification Search
CPC ................... A61B 5/150282; A61B 5/150396; A61B 5/150427; A61B 2017/06071; Y10T 29/49885; C23C 8/06; C23C 8/36; C23C 8/38; C23C 14/0042; C23C 14/5826; C23C 14/30; B21G 1/12; B21G 1/006; B21G 1/08
See application file for complete search history.

(56) References Cited

FOREIGN PATENT DOCUMENTS

| DE | 4235483 A1 * | 4/1994 | .......... A61B 5/1405 |
| JP | A-1-290786 | 11/1989 | |

(Continued)

OTHER PUBLICATIONS

May 28, 2013 International Search Report issued in PCT/JP2013/053493.

*Primary Examiner* — Jermie Cozart
(74) *Attorney, Agent, or Firm* — Oliff PLC (57) ABSTRACT Provided is a method for producing a puncture needle, which causes no significant pain during use such as when pierced. The method for producing the puncture needle includes the step of processing a pipe-like metallic base material having at one end a grinding surface obtained by machine work with plasma generated in an atmosphere filled with a mixed gas mainly including a main gas and a reaction gas.

4 Claims, 10 Drawing Sheets (51) Int. Cl.
  *C23C 8/06* (2006.01)
  *B21G 1/12* (2006.01)

(56) References Cited

FOREIGN PATENT DOCUMENTS

| JP | A-8-120470 | 5/1996 |
| JP | A-9-279331 | 10/1997 |
| JP | A-2003-225281 | 8/2003 |
| JP | A-2003-305121 | 10/2003 |
| JP | A-2003-310759 | 11/2003 |
| JP | A-2004-290410 | 10/2004 |
| JP | A-2004-358208 | 12/2004 |
| JP | A-2008-200528 | 9/2008 |
| JP | A-2009-524510 | 7/2009 |
| WO | WO 2007/083121 A1 | 7/2007 |

* cited by examiner

METHOD FOR MANUFACTURING PUNCTURE NEEDLE

TECHNICAL FIELD

The present invention relates to a puncture needle such as an injection needle, an acupuncture needle, and a suture needle and a method and an apparatus for manufacturing the same.

BACKGROUND ART

Although the size of a puncture needle such as an injection needle used for human bodies is different depending on the application, the outer diameter is usually approximately 0.3 to 1.2 mm, and there is a puncture needle having a large outer diameter of 2 mm in some cases. A 31 gauge puncture needle generally used for insulin self-injection has an outer diameter of approximately 0.25 mm. The puncture needle having such a diameter gives piercing pain and wound when pierced, whereby patients who inject themselves with insulin particularly feel fear and anxiety. Thus, it is conventionally desirable to reduce the piercing pain from a puncture needle.

One way to reduce the piercing pain from a puncture needle is to reduce the outer diameter of the needle, and a 33 gauge ultrafine needle is already commercially available as a so-called painless insulin puncture needle with reduced pain. Meanwhile, there is a puncture needle in which a taper portion is provided at a needle tube barrel portion of the puncture needle, and a diameter of a needle tip portion is made smaller than a diameter of a base end portion connected to a syringe (see, Patent Literature 1).

Meanwhile, a needle tip of a puncture needle is usually required to have a certain size that allows a volume of infusion in a needle tube to be secured. Thus, there has been requited a method of reducing pain at the time of piercing without changing a usual diameter of a needle tip. One way to reduce piercing pain from the puncture needle is to reduce frictional resistance against a living body according to surface smoothing of a needle tube. For example, a rough surface having unevenness of 10 to several ten µm that is usually observed on a surface of a medical/sanitary tool is considered to cause pain at the time of injection into the living body in the case of the puncture needle, and there is proposed to polish the surface until the surface roughness becomes approximately 1 to 20 µm (see, Patent Literature 2).

CITATION LIST

Patent Literatures

Patent Literature 1: JP 2008-200528 A
Patent Literature 2: JP 9-279331 A

SUMMARY OF INVENTION

Technical Problem

However, it is preferable to further reduce piercing pain from a puncture needle.

Solution to Problem

As a result of intensive studies to solve the above problem, the present inventors have completed the present invention.

The present invention is as follows (1) to (7).

(1) A method of manufacturing a puncture needle, including the step of processing a needle-like metallic base material, having at an end a machined surface obtained by machining, with plasma generated in an atmosphere filled with a mixed gas mainly including a main gas and a reaction gas.

(2) The method of manufacturing a puncture needle, according to (1) above, wherein a ratio (AGP/MGP) of a partial pressure of the reaction gas (AGP) to a partial pressure of the main gas (MGP) in the mixed gas is 0.01 to 0.1.

(3) The method of manufacturing a puncture needle according to (1) or (2) above, wherein in the mixed gas, the partial pressure of the main gas (MGP) is 0.3 to 0.5 Pa, and the partial pressure of the reaction gas (AGP) is 0.007 to 0.05 Pa.

(4) The method of manufacturing a puncture needle according to any of (1) to (3) above, wherein the main gas is argon, and the reaction gas is oxygen and nitrogen.

(5) The method of manufacturing a puncture needle according to any of (1) to (4) above, wherein the metallic base material includes, at an end of a pipe-like needle tube, a cut surface forming an acute angle with respect to a central axis in a longitudinal direction of the needle tube, a pair of grinding surfaces formed by grinding a front end side portion of the cut surface from the both sides line-symmetrically with respect to the central axis, and a blade edge consisting of a ridge line of tube thickness formed by crossing the pair of grinding surfaces.

(6) A puncture needle obtained by the manufacturing method according to any of (1) to (5) above.

(7) A plasma apparatus including: a vacuum chamber; a gas introducing means for introducing the mixed gas into the vacuum chamber; a holder holding the metallic base material and a filament disposed to face the holder, which are installed in the vacuum chamber; and a power supply for filament which supplies current to the filament, wherein the plasma apparatus is capable of performing the manufacturing method according to any of (1) to (5) above.

Advantageous Effects of Invention

The present invention can provide a puncture needle, which causes no significant pain during use such as when pierced, and a method and an apparatus for manufacturing the same.

DESCRIPTION OF EMBODIMENTS

The present invention will be described.

The present invention provides a method of manufacturing a puncture needle, including a process of processing a needle-like metallic base material, having at one end a machined surface obtained by machining, with plasma generated in an atmosphere filled with a mixed gas mainly including a main gas and a reaction gas.

Such a manufacturing method is hereinafter also referred to as "the manufacturing method of the present invention".
<Metallic Base Material>

First, a metallic base material in the manufacturing method of the present invention will be described.

In the manufacturing method of the present invention, the metallic base material is not limited particularly as long as it is a needle-like metallic base material having at one end a machined surface (such as a grinding surface) obtained by machining (such as machine work) and is used for obtaining a puncture needle such as an injection needle, an acupuncture needle, and a suture needle. The size and material of the metallic base material are not limited particularly as long as the metallic base material can be used as a usual injection needle, an acupuncture needle, a suture needle, or the like, and a pipe formed of stainless can be used, for example.

The type of machining is not limited especially and may be machine work (such as grinding) for obtaining a machined surface (such as a grinding surface). The plural types of machining may be performed. For example, there may be used a needle-like metallic base material having a machined surface applied to other machining such as drawing and polishing (such as blasting and stropping) in addition to the machine work.

Figure 1:
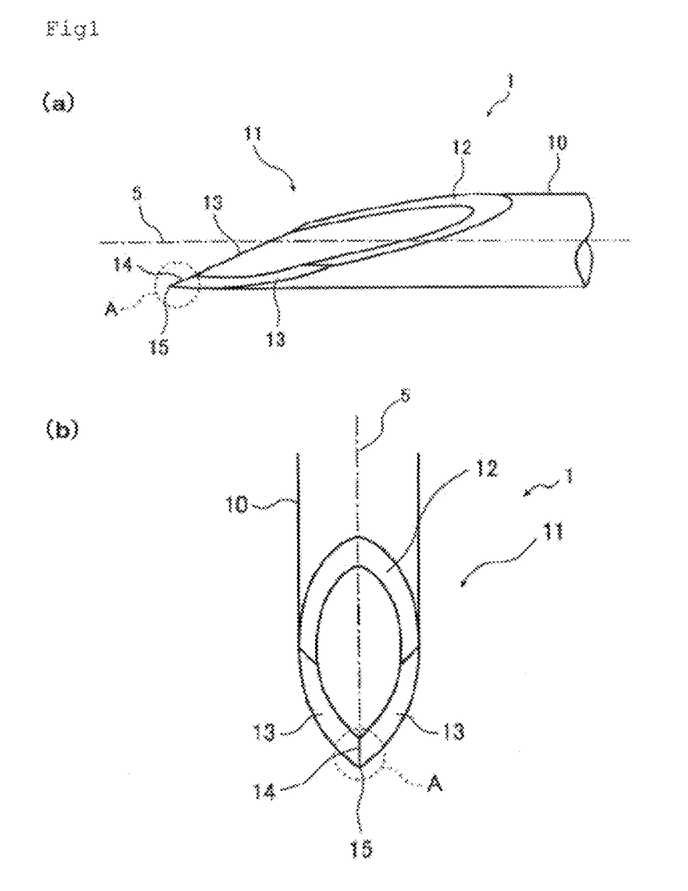
FIGS. 1(a) and 1(b) are schematic views exemplifying a shape of a metallic base material which can be used in the present invention.

The metallic base material in the manufacturing method of the present invention has a form shown in FIGS. 1(a) and 1(b), for example.

FIGS. 1(a) and 1(b) are views schematically showing an example of a shape of a blade tip in a metallic base material, FIG. 1(a) is a lateral side perspective view of a needle tip portion, and FIG. 1(b) is a front side perspective view of the needle tip portion. Although examples of a shape of a blade tip of a puncture needle include a lancet shape, a semi lancet shape, a back cut shape, and modified shapes thereof, the blade tip shown in FIGS. 1(a) and 1(b) has a lancet shape.

As exemplified in FIGS. 1(a) and 1(b), a needle tip 11 in the metallic base material has at an end of a pipe-like needle tube 10 a cut surface 12 forming an acute angle with respect to a central axis 5 in a longitudinal direction of the needle tube 10, a pair of grinding surfaces (bevel surfaces) 13 formed by grinding an about half portion on the front end side of the cut surface 12 from the both sides line-symmetrically with respect to the central axis 5, and a blade edge 14 consisting of a ridge line of tube thickness formed by crossing the pair of grinding surfaces 13. A blade A includes the blade edge 14 formed by crossing the two bevel surfaces 13 at the front end of the needle tip and a pointed blade tip 15 at the tip end of the blade edge 14. The needle tip having such a structure is reduced in contact with a skin tissue when punctured/pierced, compared with a needle tip having only a simple cut surface, and a core ring in which the skin tissue torn by a blade is incorporated in a needle tube can be structurally reduced, and piercing pain is dramatically reduced.
<Plasma Processing>

Next, plasma processing in the manufacturing method of the present invention will be described.

In the manufacturing method of the present invention, at least a machined surface (such as a grinding surface) in the metallic base material is plasma-processed.

In the plasma processing, the metallic base material is processed with plasma generated in an atmosphere filled with a mixed gas mainly including a main gas and a reaction gas.

In the conventional method, the above-described metallic base material having a machined surface obtained by machining has been processed with plasma generated in an atmosphere filled with a main gas. However, in this case, a roughness degree of a processed surface after plasma processing is high, and the present inventors have found that pain is not small when an obtained puncture needle is used. As a result of intensive studies, the present inventors have found that when the metallic base material is processed with plasma generated in an atmosphere filled with a mixed gas containing not only a main gas but also a reaction gas (preferably at a specific ratio), the roughness degree of the machined surface of the metallic base material is very small, and pain during use is dramatically reduced by sharpening a front end, and the present inventors have completed the present invention.

Although the mixed gas is mainly including a main gas and a reaction gas, the main component means that the mixed gas contains not less than 70% of the component at a volume ratio. Namely, a total concentration of the main gas and the reaction gas in the mixed gas is net less than 70 vol %. The total concentration is preferably not less than 80 vol %, more preferably 90 vol %, still more preferably 95 vol %, even more preferably 98 vol %, most preferably 99 vol %.

Although the main gas means noble gas, the main gas is preferably argon.

Although the reaction gas means a gas other than the main gas, the reaction gas is preferably oxygen and/or nitrogen.

When argon is used as the main gas, and oxygen and nitrogen are used as the reaction gas, a puncture needle with smaller pain during use is obtained, and thus it is more preferable. Accordingly, it is more preferable to use the mixed gas including argon and air.

The partial pressure of the main gas (MGP) in the mixed gas is preferably 0.01 to 10 Pa, were preferably 0.1 to 2 Pa, still more preferably 0.2 to 0.6 Pa, even more preferably 0.3 to 0.5 Pa.

The partial pressure of the reaction gas (AGP) in the mixed gas is preferably not less than 0.001 Pa, more preferably 0.001 to 1 Pa, still more preferably 0.005 to 0.1 Pa, even more preferably 0.007 to 0.05 Pa, most preferably 0.007 to 0.027 Pa.

It is preferable that the partial pressure of the main gas (MGP) in the mixed gas is 0.3 to 0.5 Pa, and the partial pressure of the reaction gas is 0.007 to 0.05 Pa. This is because a puncture needle with smaller pain during use can be obtained.

It is preferable that the pressure of the mixed gas when generating plasma is preferably 0.1 to 10 Pa, more preferably 0.2 to 1.2 Pa, still more preferably 0.3 to 0.8 Pa, even more preferably 0.307 to 0.55 Pa.

It is preferable that in the mixed gas, a ratio (AGP/MGP) of the partial pressure of the reaction gas (AGP) to the partial pressure of the main gas (MGP) is preferably 0.01 to 0.5, more preferably 0.01 to 0.1, still more preferably 0.01 to 0.08, even more preferably 0.02 to 0.1, most preferably 0.023 to 0.054. This is because a puncture needle with smaller pain during use can be obtained.

As described above, although it is preferable to use the mixed gas including argon and air, in this case the partial pressure of argon in the mixed gas is preferably 0.01 to 10 Pa, more preferably 0.1 to 2 Pa, still more preferably 0.2 to 0.6 Pa, even more preferably 0.3 to 0.5 Pa. Meanwhile, the partial pressure of air in the mixed gas is preferably not less than 0.001 Pa, more preferably 0.001 to 1 Pa, still more preferably 0.005 to 0.1 Pa, even more preferably 0.006 to 0.05 Pa, especially preferably 0.007 to 0.05 Pa, most preferably 0.006 to 0.027 Pa.

Figure 2:
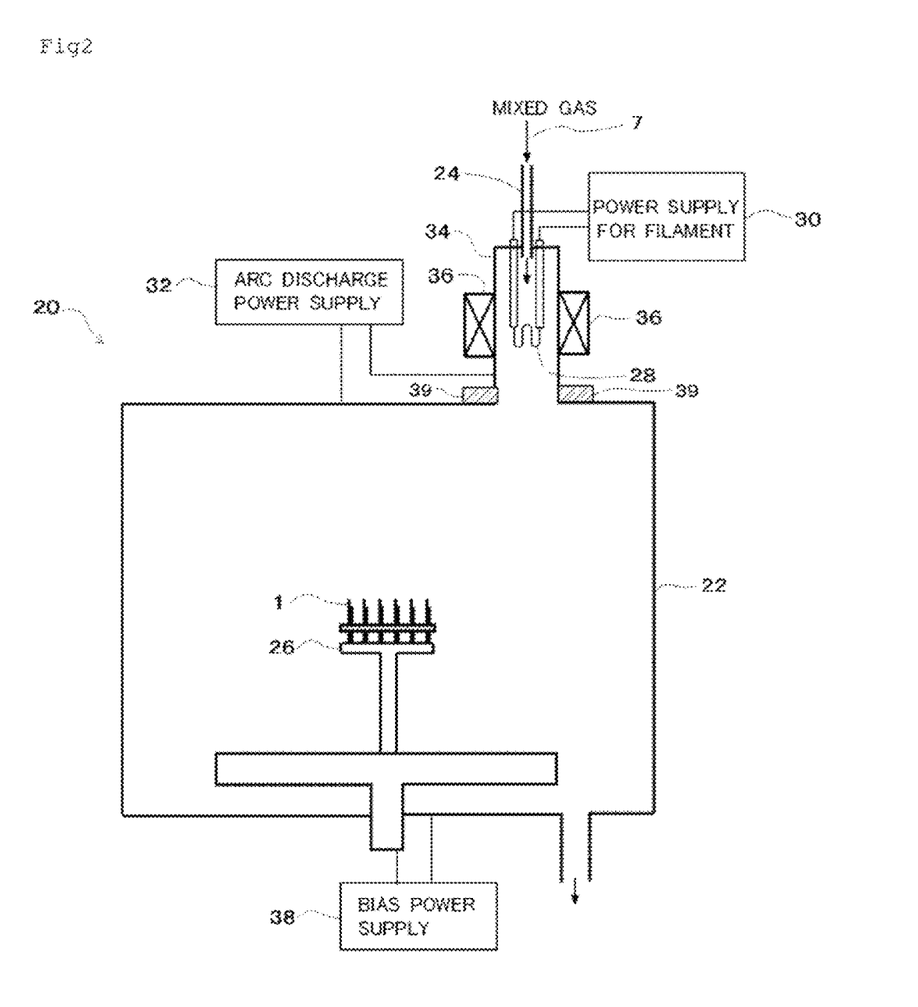
FIG. 2 is a schematic cross-sectional view of a plasma apparatus in which the manufacturing method of the present invention can be preferably performed.

It is preferable that the metallic base material is plasma-processed by an apparatus shown in FIG. 2.

FIG. 2 shows a plasma apparatus capable of performing an arc discharge hot filament method. A plasma apparatus 20 in FIG. 2 is provided with a vacuum chamber 22; a gas introducing means 24 for introducing a mixed gas 7 into the vacuum chamber 22; a holder 26 holding a base material 1 and a filament 28 disposed to face the holder 26, which are installed in the vacuum chamber; and a power supply 30 for filament which supplies current to the filament 26. The plasma apparatus 20 is further provided with a hollow cathode electrode 34 installed to cover the filament 28 and provided with an arc discharge power supply 32, a coil 36 installed on an outer surface of the hollow cathode electrode 34, and a bias voltage power supply 38 capable of applying bias voltage to the base material 1.

In such a plasma apparatus 20, a mixed gas mainly including a main gas and a reaction gas is introduced into the vacuum chamber 22 by using the gas introducing means 24 to fill the inside of the vacuum chamber 22, and thereafter, current is supplied to the filament 28, whereby glow discharge is generated, so that plasma of discharge gas can be generated.

The bias voltage is preferably 50 to 1000 V, more preferably 100 to 800 V, still more preferably 300 to 600 V.

Plasma processing time is preferably 1 to 50 hours, more preferably 1 to 10 hours, still more preferably 1.5 to 4 hours, even more preferably 2 to 3 hours.

Ion current density is preferably 0.1 to 50 mA/cm$^2$, more preferably 0.5 to 10 mA/cm$^2$, still more preferably 1 to 2 mA/cm$^2$.

In the partial pressure of the main gas (MGP) and the partial pressure of the reaction gas (AGP) in the manufacturing method of the present invention, when the mixed gas 7 is introduced into the vacuum chamber 22 by the gas introducing means 24, the flow rates of the main gas and the reaction gas are measured by using a flowmeter (such as an orifice flowmeter), and the partial pressure of the main gas (MGP) and the partial pressure of the reaction gas (AGP) can be calculated from the measured values and the volume of the vacuum chamber 22.

The pressure of the mixed gas can be obtained as a total of the partial pressures of the main gas and the reaction gas measured and calculated as described above.

EXAMPLES

Example 1

An SUS304 needle tube (29 G, outer diameter: 0.3 mm) was ground and subjected to drawing, and a metallic base material having the needle tip 11 shown in FIGS. 1(a) and 1(b) was produced. Then, machining such as electrolytic polishing was not applied to the metallic base material, the metallic base material was installed on a holder loaded in a plasma generating apparatus having a structure shown in FIG. 2, and the needle tip was plasma-processed. In the plasma processing, as the plasma generating apparatus, an arc discharge hot filament method plasma generating apparatus (PINK type, manufactured by Nagata Seiki Co., Ltd.) was used, a discharge gas was a mixed gas including argon and air (Ar gas partial pressure=0.4 Pa, air partial pressure=0.027 Pa), and the plasma processing was performed for 2.5 hours under such conditions that the ion current density was 1.5 mA/cm$^2$ and the bias voltage was 400 V.

Although a plurality of needles were plasma-processed simultaneously, the needles are installed on the holder while being separated by 5 mm to prevent from overlapping each other.

Figure 3:
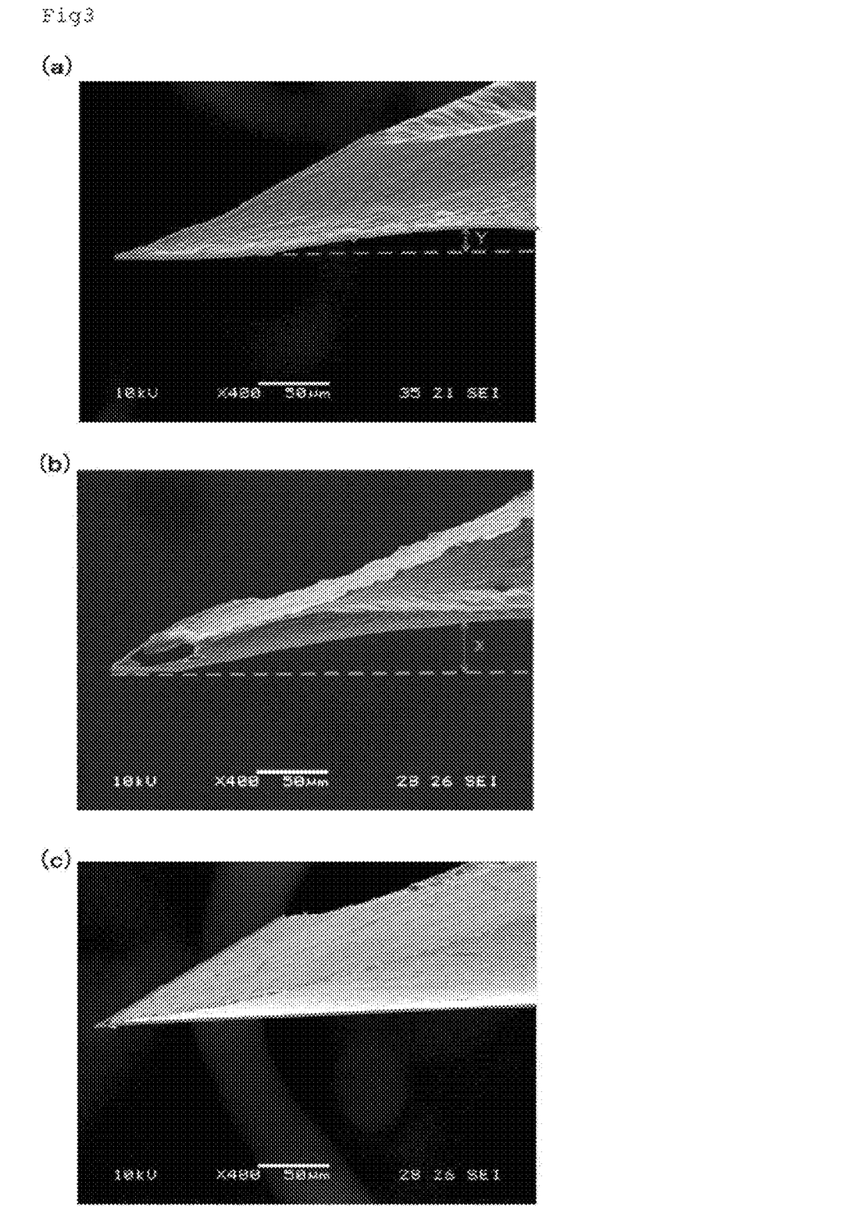
FIGS. 3(a) to 3(c) are images (magnified photographs) obtained by observing needle tips, obtained by Example 1 and Comparative Examples 1 and 2, using a scanning electron microscope (SEM).
Figure 4:
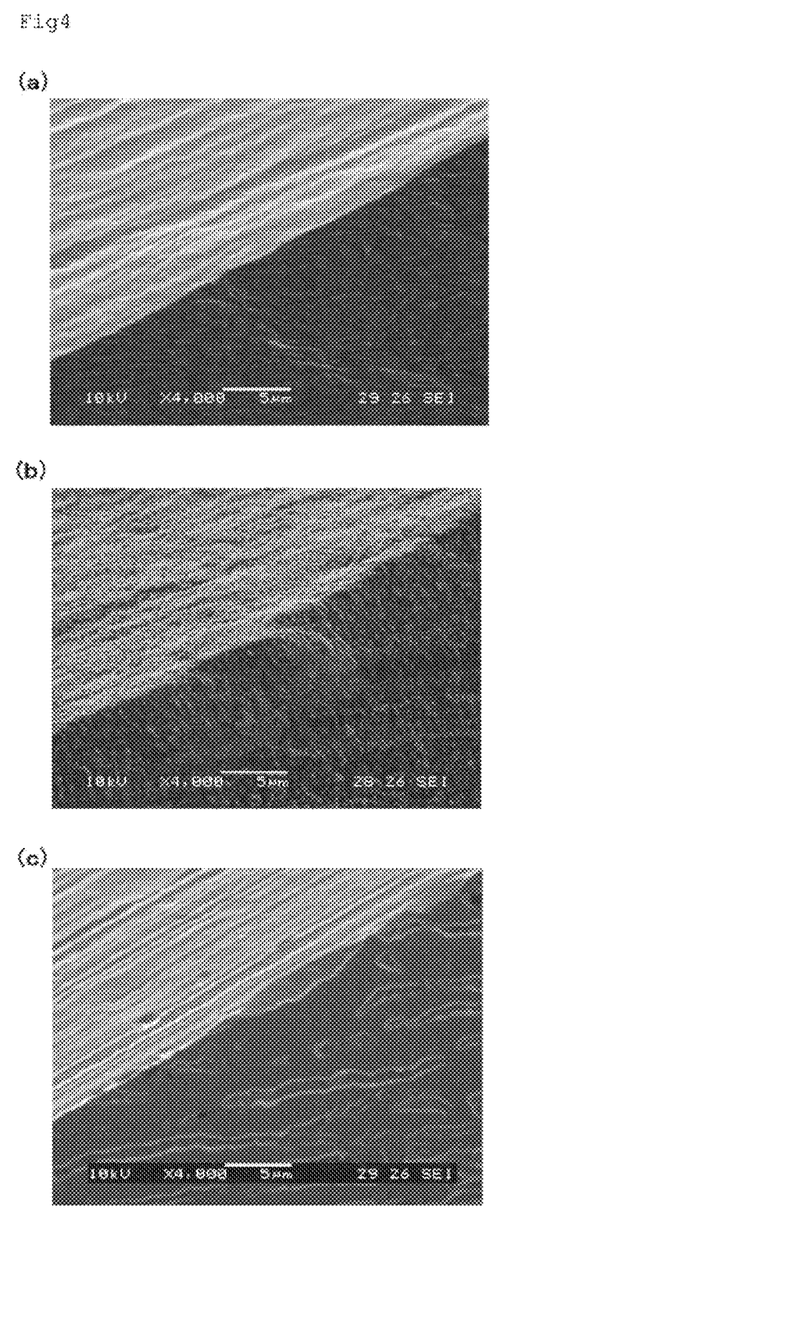
FIGS. 4(a) to 4(c) are other images (magnified photographs) obtained by observing needle tip ridge portions, obtained by Example 1 and Comparative Examples 1 and 2, using the scanning electron microscope (SEM).

Then, the needle tip after the plasma processing was observed by using a scanning electron microscope (SEM). Obtained magnified photographs are shown in FIGS. 3(a) and 4(a). FIGS. 3(a) to 3(c) are images (photographs) of the needle tip magnified 400 times, and FIGS. 4(a) to 4(c) are images (photographs) of a bevel surface corner portion magnified 4000 times.

The processing conditions and the like are shown in Table 1.

Example 2

In Example 1, the partial pressure of argon in the discharge gas was 0.4 Pa, and the partial pressure of air was 0.027 Pa; however, in Example 2, the partial pressure of argon was 0.4 Pa, and the partial pressure of air was 0.006 Pa. With the exception of this point, the plasma processing was performed in the same manner as Example 1.

The processing conditions and the like are shown in Table 1.

Example 3

In Example 1, the partial pressure of argon in the discharge gas was 0.4 Pa, and the partial pressure of air was 0.027 Pa; however, in Example 3, the partial pressure of argon was 0.4 Pa, and the partial pressure of air was 0.05 Pa. With the exception of this point, the plasma processing was performed in the same manner as Example 1.

The processing conditions and the like are shown in Table 1.

Comparative Example 1

In Example 1, although the mixed gas including argon (partial pressure: 0.4 Pa) and air (partial pressure: 0.027 Pa)

was used as the discharged gas, in Comparative Example 1 argon (100 vol %) was used as the discharge gas. With the exception of this point, the plasma processing was performed in the same manner as Example 1.

Then, as in Example 1, the needle tip after plasma-processing was observed by using the scanning electron microscope (SEM). Obtained magnified photographs are shown in FIGS. 3(b) and 4(b).

The processing conditions and the like are shown in Table 1.

TABLE 1

| Description of case | Example 1 Plasma obtained by adding air to Ar | Example 2 Plasma obtained by adding air to Ar | Example 3 Plasma obtained by adding air to Ar | Comparative Example 1 obtained by Ar only |
|---|---|---|---|---|
| Needle material | 29G | 29G | 29G | 29G |
| Air pressure [Pa] | 0.027 | 0.006 | 6.05 | Not detected |
| Ar gas pressure [Pa] | 0.4 | 0.4 | 0.4 | 0.4 |
| Mixed gas pressure [Pa] | 0.427 | 0.406 | 0.45 | 0.4 |
| Ion current density [mA/cm$^2$] | 1.5 | 1.5 | 1.5 | 1.5 |
| Bias voltage value [V] | 400 | 400 | 400 | 400 |
| Processing time [Hr] | 1.5 | 1.5 | 1.5 | 1.5 |
| Distance between needles [mm] | 5 | 5 | 5 | 5 |
| AGP/MGP (calculated value | 0.068 | 0.015 | 0.125 | 0 |

Comparative Example 2

As in Example 1, an SUS304 needle tube (29 G, outer diameter: 0.3 mm) was ground and subjected to drawing, and a metallic base material having the lancet shape needle tip 11 shown in FIGS. 1(a) and 1(b) was produced. Then, phosphoric acid was used as a drug solution, and a current oil 10 V was charged to apply electrolytic polishing.

Then, the needle tip after electrolytic polishing was observed by using the scanning electron microscope (SEM). Obtained magnified photographs are shown in FIGS. 3(c) and 4(c).

Comparing FIG. 3(b) with FIG. 3(c), it can be considered that; the needle tip (FIG. 3(b)) obtained in Comparative Example 1 is more sharpened than the needle tip (FIG. 3(c)) obtained in Comparative Example 2. However, comparing FIG. 4(a) with FIG. 4(b), it can be considered that a surface of the needle tip (FIG. 4(b)) obtained in Comparative Example 1 is rougher than a surface of the needle tip (FIG. 4(a)) obtained in Example 1. Accordingly, comparing the needle tip obtained in Comparative Example 1 with that in Example 1, it can be considered that piercing resistance is high.

Comparing FIG. 4(a) with FIG. 4(c), it can be considered that the smoothness of the needle tip (FIG. 4(a)) obtained in Example 1 is higher than the smoothness of the needle tip (FIG. 4(c)) obtained in Example 2. Accordingly, it can be considered that in the needle obtained in Example 1, resistance during use is further reduced, and a sense of discomfort during drawing of the needle is further reduced.

Comparing FIG. 3(b) with FIG. 3(c), it can be considered that the shape of the front end of the needle tip (FIG. 3(b)) obtained in Comparative Example 1 is abnormally deformed to be depressed. Consequently, it can be considered that the needle tip obtained in Comparative Example 1 is abnormally high in primary resistance value in the piercing resistance.

On the other hand, although the needle tip obtained in Example 1 shown an FIG. 3(a) is deformed to be depressed, the degree of depressed deformation is not abnormal. In order to measure the degree of depressed deformation in Example 1 and Comparative Example 1, when the degree of depressed deformation from the front end at the same distance (=200 μm) in these examples was measured as the amount of displacement with respect to the case of Comparative Example 2 (FIG. 3(c)) free from depressed deformation (Y in FIG. 3(a) and X in FIG. 3(b)), Y=16 μm in Example 1, and X=35 μm in Comparative Example 1.

In a puncture needle, piercing pain can be generally evaluated by the piercing resistance when the needle tip punctures a predetermined material. For example, in the lancet shape puncture needle shown in FIGS. 1(a) and 1(b), the piercing resistance during passage of the blade edge 14 is referred to as primary resistance, the resistance during passage of a polishing surface 13 is referred to as secondary resistance, the resistance during passage of the cut surface 12 is referred to as tertiary resistance, and the piercing pain can be evaluated by the magnitude of each resistance.

The surface smoothness of each of the needle tips obtained in Examples 2 and 3 was higher than that of the needle tip obtained in Comparative Example 1 (FIG. 4(b)). Accordingly, it can be considered that the piercing resistance of the needle tip obtained in Comparative Example 1 is higher than those of Examples 2 and 3. Accordingly, it can be considered that comparing with the needle tip obtained in Comparative Example 1, in the needle tips obtained in Examples 2 and 3, the resistance during use is further reduced, and a sense of discomfort during drawing of the needle is further reduced.

However, the surface smoothness of the needle tip obtained in Example 1 was higher than those of the needle tips obtained in Examples 2 and 3. Accordingly, it can be considered that the needle tip obtained in Example 1 is more preferable than the needle tips obtained in Examples 2 and 3.

Next, a commercially available needle obtained by coating silicone onto the needle tip after machining and electrolytic polishing as in Comparative Example 2 was prepared, and piercing resistance values of this needle and the needle obtained in Example 1 were measured.

In the measurement of the piercing resistance value, an autograph (50 N) was used. There was used a polyethylene sheet having a thickness of 0.05 mm and having a hardness of A50 that was measured by using a rubber hardness meter (durometer) conforming to JIS-K6253 type A, and a load was measured when the puncture needle was punctured under such conditions that the lead was 50 N, the rate was 1.0 mm/min, and the stroke was 3 mm. Each ten needle was measured, and an average value was obtained.

Figure 5:
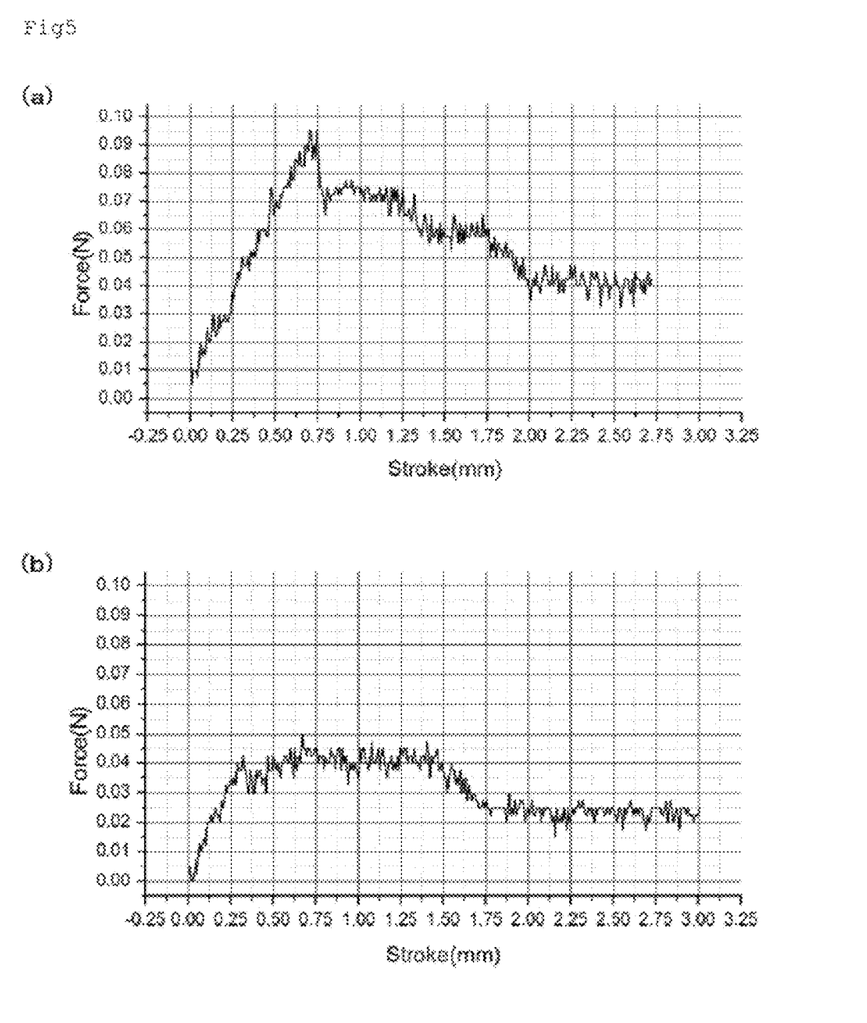
FIGS. 5(a) and 5(b) are graphs showing piercing resistance values of a puncture needle obtained in Example 1.

The result of measurement of the piercing resistance value (average value of ten needles) obtained when the commercially available needle is used is shown in FIG. 5(a), and the result of measurement of the piercing resistance value (average value off ten needles) obtained when the needle obtained in Example 1 is used is shown in FIG. 5(b).

Comparing FIG. 5(a) with FIG. 5(b), while the maximum value of the piercing resistance is 0.09 N in the commercially available needle (FIG. 5(a)), the maximum value of the piercing resistance is 0.05 N in the needle (FIG. 5(b)) obtained in Example 1, and it is found that the maximum value is significantly reduced. Consequently, in the needle of Example 1 corresponding to the present invention, although the needle is not coated with silicone, it could be confirmed that the piercing resistance can be reduced compared with the case where the needle was coated with silicone.

Example 4

Figure 6:
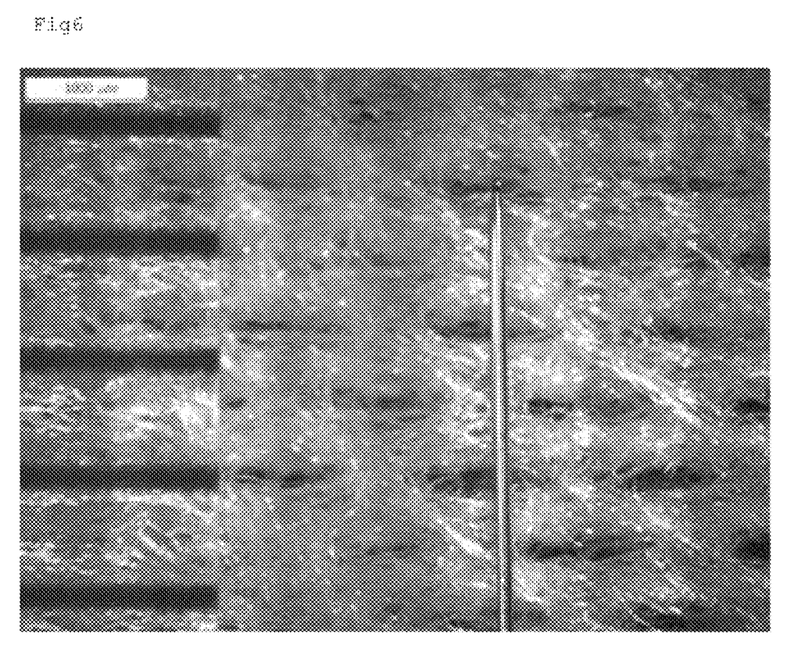
FIG. 6 is a magnified photograph of an acupuncture needle used in Examples 4 and 5.

An SUS 304 acupuncture needle (diameter: 0.14 mm, entire length: 60 mm, only one end has a sharp-pointed portion) shown in FIG. 6 was prepared. The scale (unit length) shown in FIG. 6 is 1000 μm.

The needle was installed on the holder loaded in the plasma generating apparatus having a structure shown in FIG. 2, and the needle tip was plasma-processed. In the plasma processing, the plasma generating apparatus similar to that in Example 1 was used, a mixed gas including air and argon (air:argon (volume ratio)=3:97) was used as a discharge gas, and the plasma processing was performed for two hours under such conditions that the discharge current value was 40 A, and the bias voltage was 400 V.

Although a plurality of acupuncture needles were plasma-processed simultaneously, the needles were installed on the holder while being separated by 5 mm to prevent from overlapping each other.

Figure 7:
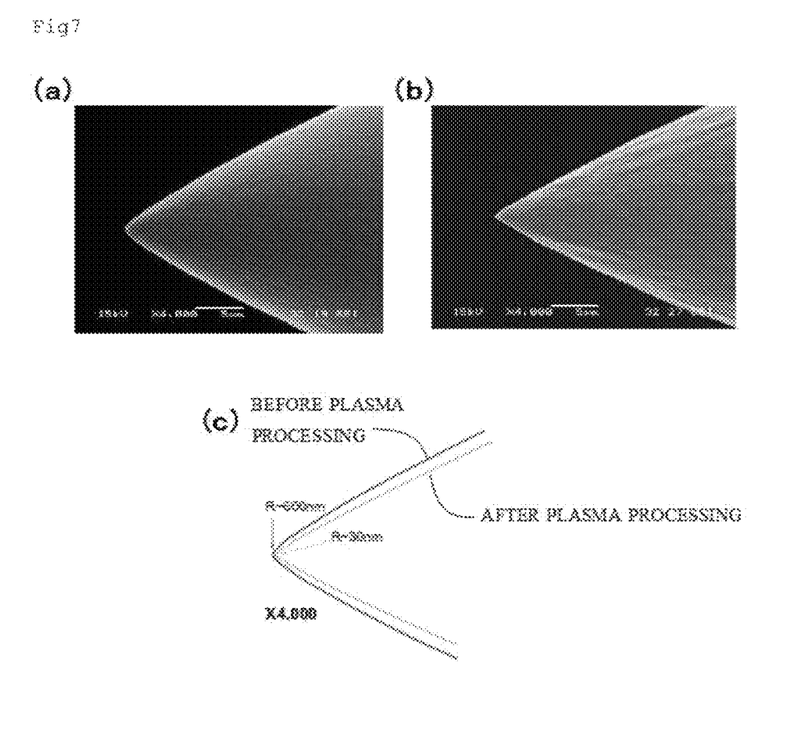
FIGS. 7(a) and 7(b) are images (magnified photographs) obtained by observing a needle tip, obtained by Example 4, using the scanning electron microscope (SEM).

Then, the needle tip after the plasma processing was observed by using a scanning electron microscope (SEM) (JEOL JSM-5510, manufactured by JEOL Ltd.). The magnification was 4000 times. An obtained magnified photograph is shown in FIG. 7(b). FIG. 7(a) is a magnified photograph obtained by observing the needle tip before the plasma processing at the same magnification, using a similar SEM. FIG. 7(c) is a view for comparing outer shapes (profiles) of the needle tips obtained from FIGS. 7(a) and 7(b).

When a curvature radius of the needle tip before and after the plasma processing was measured by using FIGS. 7(a) to 7(c), it was found that while the curvature radius of the needle tip before the plasma processing (FIG. 7(a)) was 600 nm, the curvature radius of the needle tip after the plasma processing (FIG. 7(b)) was 30 nm. Consequently, it could be confirmed that the needle tip was sharpened by the plasma processing.

Example 5

Figure 8:
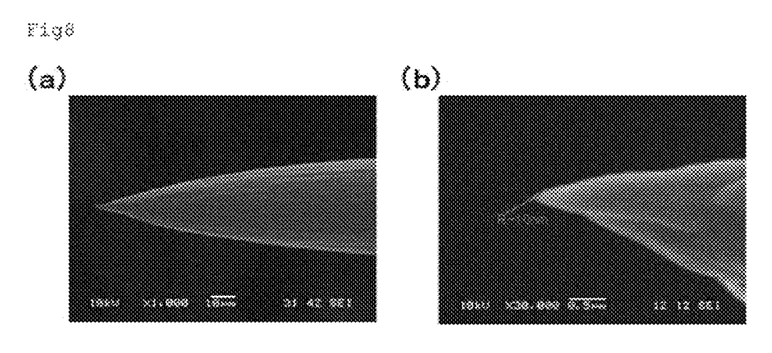
FIGS. 8(a) and 8(b) are images (magnified photographs) obtained by observing a needle tip, obtained by Example 5, using the scanning electron microscope (SEM).

Although the plasma processing was performed for two hours in Example 4, the plasma processing was performed for seven hours in Example 5, and with the exception of this point, the plasma processing was performed in the same manner as Example 4. The obtained needle tip after the plasma processing was observed by using a SEM similar to that in Example 4, and magnified photographs were obtained. FIG. 8(a) is a magnified photograph of the needle tip magnified 1000 times, and FIG. 8(b) is a magnified photograph of the same needle tip magnified 30000 times.

When the curvature radius of the needle tip after the plasma processing was measured by using FIGS. 8(a) and 8(b), it was found that the curvature radius was 10 nm.

As described in Example 4, while the curvature radius of the needle tip before the plasma processing was 600 nm, the curvature radius of the needle tip after the plasma processing obtained in Example 5 was 10 nm. Namely, it could be confirmed that the needle tip was sharpened by the plasma processing in the present invention.

Next, there were measured the piercing resistance values of three needles including the SUS 304 acupuncture needle (before plasma processing) shown in FIG. 6, the puncture needle obtained by being plasma-processed in Example 4 shown in FIGS. 7(a) to 7(c), and the puncture needle obtained by being plasma-processed in Example 5 shown in FIGS. 8(a) and 8(b).

In the measurement of the piercing resistance value, a surface measuring instrument HEIDON 14DR manufactured by Shinto Scientific Co., Ltd. was used. A change of a resistance value was measured when a puncture needle was pierced into a silicone film having a thickness of 0.05 mm at a rate of 50 mm/min.

Figure 9:
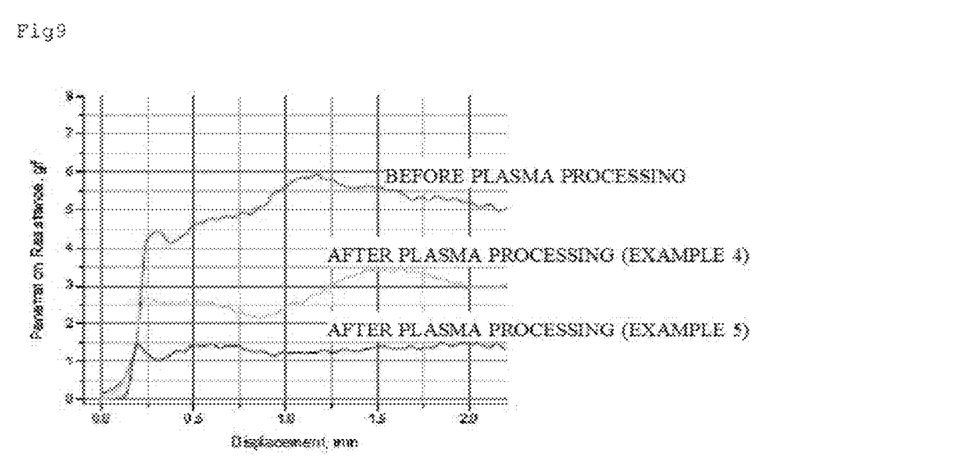
FIG. 9 is a graph showing the piercing resistance values measured in Examples 4 and 5.

The result of measurement of the piercing resistance value is shown in FIG. 9. In FIG. 9, the X-axis shows a piercing amount (depth: mm), and the Y-axis shows the piercing resistance value (gf).

Figure 10:
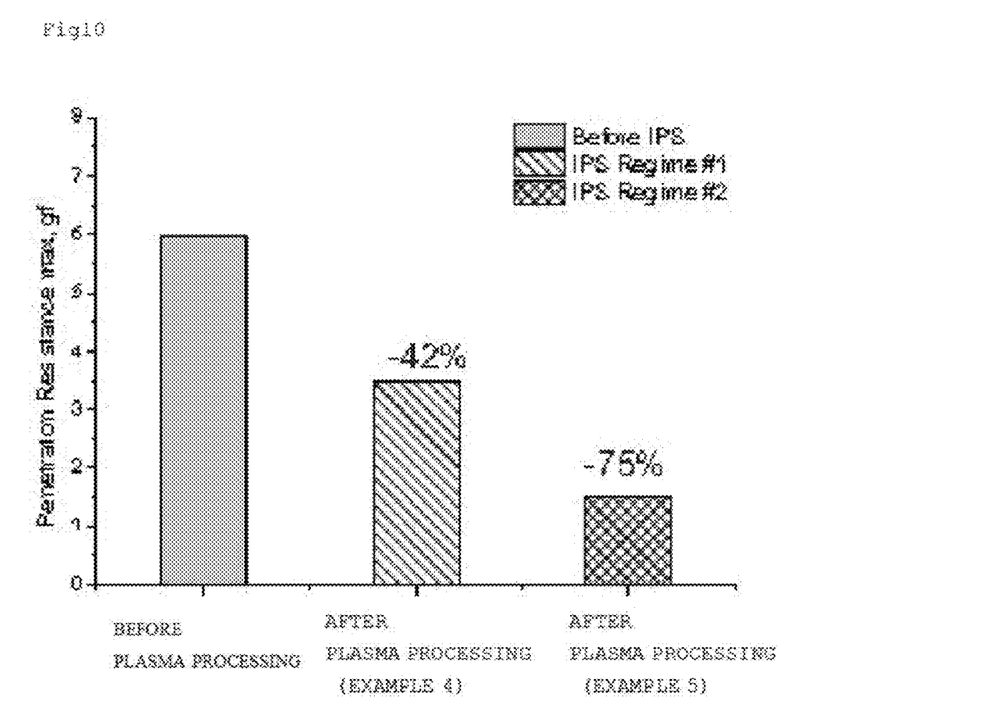
FIG. 10 is a graph comparing maximum piercing resistance values measured in Examples 4 and 5.

The maximum piercing resistance value in each needle obtained from FIG. 9 is shown in FIG. 10.

As seen in FIG. 9, the piercing resistance of the puncture needle obtained by being plasma-processed in Example 4 is lower than that of the SUS 304 acupuncture needle (before plasma processing), and the piercing resistance of the puncture needle obtained by being plasma-processed in Example 5 is further lower.

As seen in FIG. 10, when the maximum piercing resistance value in the SUS 304 acupuncture needle (before plasma processing) is 100%, the maximum piercing resistance value in the puncture needle obtained by being plasma-processed in Example 4 is lower by 42%, and the maximum piercing resistance value in the puncture needle obtained by being plasma-processed in Example 5 is lower by 75%.

Although Examples 4 and 5 are experiments on acupuncture needles, the present inventors confirmed that similar results are obtained in suture needles. The suture needle mainly has a fishhook-shaped hook, and the front end is usually machined into a lancet shape.

Experiment 1

A rectangular plate-shaped sample (10 mm×10 mm, thickness: 5 mm) formed of SUS 304 and having a mirror-finished main surface was prepared. Such a sample having a mirror surface is hereinafter also referred to as a rectangular test piece.

Next, the rectangular test piece was installed on a holder loaded in a plasma generating apparatus having a structure shown in FIG. 2. In this case, the rectangular test piece was installed on the holder so that the outermost surface on the filament 28 side in the holder and a mirror-finished main surface (hereinafter also referred to as a mirror surface) of the rectangular test piece are substantially coplanar with each other. When the rectangular test piece is thus installed on the holder, it is possible to suppress concentration of plasma on an end surface of the rectangular test piece.

Next, the mirror surface of the rectangular test piece was plasma-processed. In the plasma processing, the plasma generating apparatus similar to that in Example 1 was used, a mixed gas including argon and air (total pressure=0.4 Pa, air in the mixed gas=10 vol %) was used as a discharge gas, and the plasma processing was performed for 45 hours under such conditions that the discharge current was 40 A, and the bias voltage was 400 V. The temperature of the rectangular test piece during the plasma processing was 250° C.

The processing conditions and the like are shown in Table 2.

Next, the mirror surface of the rectangular test piece after the plasma-processing was observed by using an atomic force microscope (model number: NPX100 manufactured by Seiko Instruments Inc.). An obtained AFM photographs are shown in FIGS. 11(a) and 11(b).

Further, the mirror surface of the rectangular test piece after the plasma-processing was observed by using a scanning electron microscope (SEM). Obtained magnified photographs are shown in FIGS. 13(a) and 13(b). FIG. 13(a) is an image (photograph) of a needle tip magnified 4000 times, and FIG. 13(b) is an image (photograph) of the mirrored surface magnified 10000 times.

Furthermore, the mirror surface of the rectangular test piece after the plasma-processing was analyzed by using an Auger electron spectroscopy analyzer (model number: JAMP-9500F manufactured by JEOL).

Figure 15:
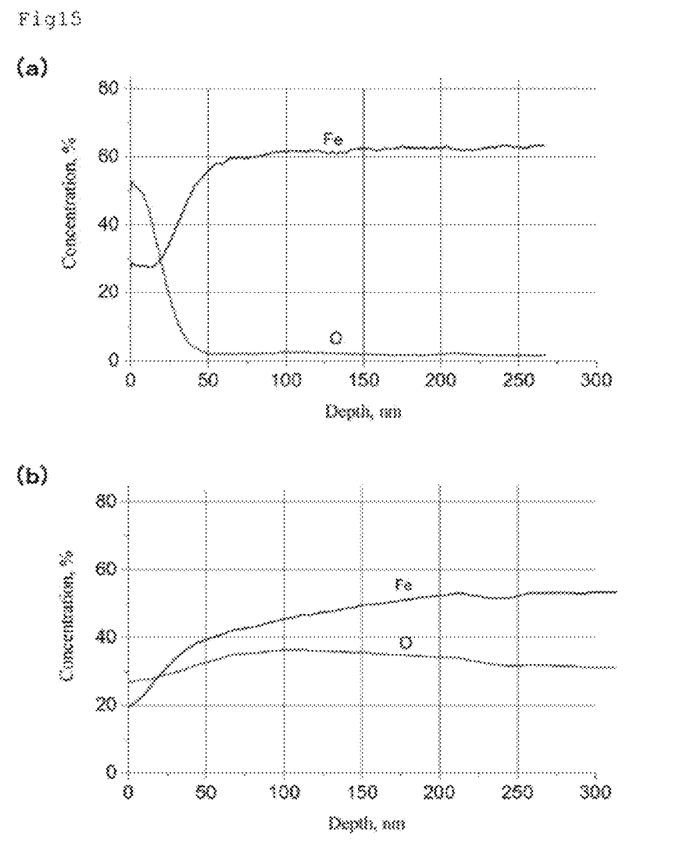
FIGS. 15(a) and 15(b) are graphs showing results of analysis of the mirror surfaces of the rectangular test pieces, processed by Experiments 1 and 2, using an Auger electron spectroscopy analyzer.

The results of the analysis are shown in FIG. 15(a).

Experiment 2

A rectangular test piece having a mirror surface was produced by being processed in the same manner as in Experiment 1. Then, a plasma generating apparatus similar to that in Experiment 1 was used, the rectangular test piece was similarly installed on a holder, and the mirror surface of the rectangular test piece was plasma-processed. However, argon (total pressure=0.4 PA) was used as a discharge gas, and the plasma processing was performed for four hours under such conditions that the discharge current was 40 A, and the bias voltage was 400 V.

When weight reduction of the rectangular test piece due to the plasma processing was measured with a precision balance, it was confirmed that the weight reduction per unit time was similar to that in Experiment 1. Although the discharge gas contains a slight amount of air, it was confirmed that the amount was not more than 0.25 vol %. A temperature of the rectangular test piece during the plasma processing was 240° C.

The processing conditions and the like are shown in Table 2.

Figure 12:
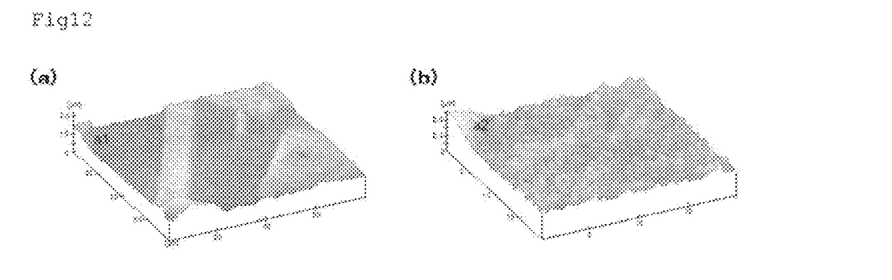
FIGS. 12(a) and 12(b) are AFM photographs obtained in Experiment 2.

Next, the mirror surface of the rectangular test piece after the plasma processing was observed by using an atomic force microscope similar to that in Experiment 1. An obtained AFM photograph is shown in FIG. 12.

As in Experiment 1, the mirror surface of the rectangular test piece after the plasma processing was observed by using the scanning electron microscope (SEM). Obtained magnified photographs are shown in FIGS. 14(a) and 14(b). FIG. 14(a) is an image (photograph) of a needle tip magnified 4000 times, and FIG. 14(b) is an image (photograph) of the mirror surface magnified 10000 times.

Further, the mirror surface of the rectangular test piece after the plasma processing was analyzed by using an Auger electron spectroscopy analyzer similar to that in Experiment 1.

The results of the analysis are shown in FIG. 15(b).

TABLE 2

|  | Experiment 1 | Experiment 2 |
| --- | --- | --- |
| Total pressure mixed gas [Pa] | 0.4 | 0.4 |
| Volume of air in mixed gas [vol %] | 10 | <0.25 |
| Discharge current [A] | 40 | 40 |
| Bias voltage value [V] | 400 | 400 |
| Sample temperature [° C.] | 250 | 240 |

Figure 11:
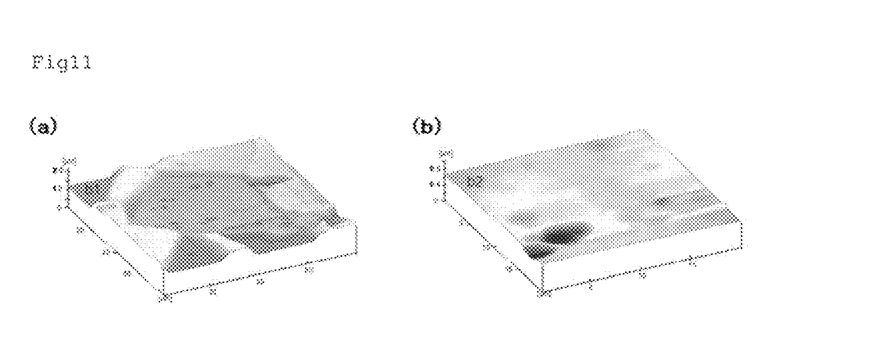
FIGS. 11(a) and 11(b) are AFM photographs obtained in Experiment 1.

As seen in FIGS. 11(a) to 12(b), the surface smoothness in Experiment 1 (FIGS. 11(a) and 11(b)) is higher than the surface smoothness in Experiment 2 (FIGS. 12(a) and 12(b)) (the surface in Experiment 1 is smoother than the surface in Experiment 2).

Figure 13:
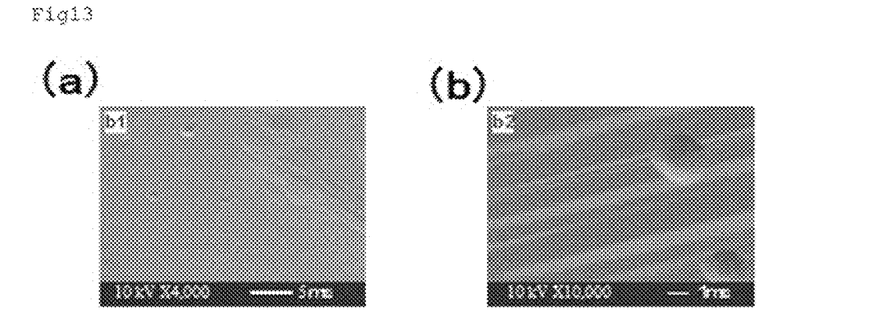
FIGS. 13(a) and 13(b) are images (magnified photographs) obtained by observing a mirror surface of a rectangular test piece processed by Experiment 1, using the scanning electron microscope (SEM).
Figure 14:
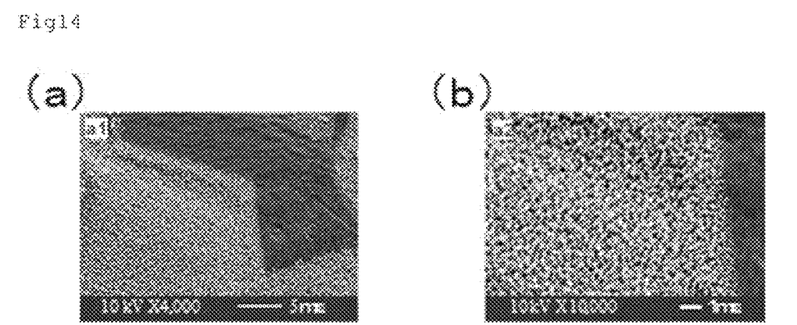
FIGS. 14(a) and 14(b) are images (magnified photographs) obtained by observing a mirror surface of a rectangular test piece processed by Experiment 2, using the scanning electron microscope (SEM).

Similarly, as seen in FIGS. 13(a) to 14(b), the surface smoothness in Experiment 1 (FIGS. 13(a) and 13(b)) is higher than the surface smoothness in Experiment 2 (FIGS. 14(a) and 14(b)) (the surface in Experiment 1 is smoother than the surface in Experiment 2).

As seen in FIGS. 15(a) and 15(b), an oxygen concentration in a mirror surface portion of the rectangular test piece in Experiment 1 (FIG. 15(a)) is higher than that in Experiment 2 (FIG. 15(b)).

Comparing Experiment 1 with Experiment 2, it was found that in the present invention using a mixed gas including argon and air as a discharge gas, the surface smoothness of a needle tip and a needle tube portion is high compared to the case of using argon as the discharge gas, and when the present invention is used as an injection needle, the piercing resistance is reduced.

REFERENCE SIGNS LIST 1 metallic base material
10 needle pipe
11 needle tip
12 cut surface
13 grinding surface (bevel surface)
14 blade edge
15 needle tip
20 plasma apparatus
22 vacuum chamber
24 gas introducing means
26 holder
28 filament
30 power supply for filament
32 arc discharge power supply
34 hollow cathode electrode
36 coil
38 bias voltage power supply
39 insulator
7 mixed gas

The invention claimed is:

1. A method of manufacturing a puncture needle, comprising the step of processing a needle-like metallic base material, having at an end a machined surface obtained by machining, with plasma generated in an atmosphere filled with a mixed gas mainly including a main gas and a reaction gas,
    wherein in the mixed gas, the partial pressure of the main gas (MGP) is 0.3 to 0.5 Pa, and the partial pressure of the reaction gas (AGP) is 0.007 to 0.05 Pa; and
    the main gas is argon, and the reaction gas is oxygen and nitrogen.

2. The method of manufacturing a puncture needle according to claim 1, wherein a ratio (AGP/MGP) of a partial pressure of the reaction gas (AGP) to a partial pressure of the main gas (MGP) in the mixed gas is 0.01 to 0.1.

3. The method of manufacturing a puncture needle according to claim 2, wherein the metallic base material comprises, at an end of a pipe-like needle tube, a cut surface forming an acute angle with respect to a central axis in a longitudinal direction of the needle tube, a pair of grinding surfaces formed by grinding a front end side portion of the cut surface from the both sides line-symmetrically with respect to the central axis, and a blade edge comprising a ridge line of tube thickness formed by crossing the pair of grinding surfaces.

4. The method of manufacturing a puncture needle according to claim 1, wherein the metallic base material comprises, at an end of a pipe-like needle tube, a cut surface forming an acute angle with respect to a central axis in a longitudinal direction of the needle tube, a pair of grinding surfaces formed by grinding a front end side portion of the cut surface from the both sides line-symmetrically with respect to the central axis, and a blade edge comprising a ridge line of tube thickness formed by crossing the pair of grinding surfaces.

* * * * *